(12) United States Patent
Lee et al.

(10) Patent No.: US 11,793,647 B2
(45) Date of Patent: Oct. 24, 2023

(54) ACETABULAR APPARATUSES FOR HIP REVISION SURGERY

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Stephen J. Lee, Memphis, TN (US); Jeffrey J. Shea, Memphis, TN (US)

(73) Assignees: Smith & Nephew, Inc., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 220 days.

(21) Appl. No.: 17/442,498

(22) PCT Filed: Mar. 24, 2020

(86) PCT No.: PCT/US2020/024450
§ 371 (c)(1),
(2) Date: Sep. 23, 2021

(87) PCT Pub. No.: WO2020/198219
PCT Pub. Date: Oct. 1, 2020

(65) Prior Publication Data
US 2022/0151792 A1 May 19, 2022

Related U.S. Application Data

(60) Provisional application No. 62/823,343, filed on Mar. 25, 2019.

(51) Int. Cl.
*A61F 2/34* (2006.01)
*A61F 2/30* (2006.01)

(52) U.S. Cl.
CPC ............ *A61F 2/34* (2013.01); *A61F 2/30734* (2013.01); *A61F 2002/3069* (2013.01);
(Continued)

(58) Field of Classification Search
CPC ......................................................... A61F 2/34
See application file for complete search history.

(56) References Cited

U.S. PATENT DOCUMENTS

| 5,931,870 A | 8/1999 | Cucklet et al. |
| 6,416,553 B1 | 7/2002 | White et al. |

(Continued)

FOREIGN PATENT DOCUMENTS

EP   3033050 A1   6/2016

OTHER PUBLICATIONS

International Search Report and Written Opinion for International Application No. PCT/US2020/024450, dated Jun. 5, 2020.

(Continued)

*Primary Examiner* — Brian A Dukert
(74) *Attorney, Agent, or Firm* — KDW Firm PLLC

(57) ABSTRACT

Prostheses, acetabular apparatuses, and methods of use are disclosed. In some embodiments, an acetabular apparatus includes an acetabular cup and an acetabular cage disposed within an interior of the acetabular cup. The acetabular cage may include a central portion including a first section and a second section rotatably coupled together, and a first flange extending from the first section and a second flange extending from the second section. The acetabular prosthesis may further include a fastener extending through each of the acetabular cup and the central portion of the acetabular cage.

21 Claims, 12 Drawing Sheets

(52) U.S. Cl.
CPC . *A61F 2002/3403* (2013.01); *A61F 2002/343* (2013.01); *A61F 2002/3406* (2013.01); *A61F 2002/3408* (2013.01); *A61F 2002/3432* (2013.01)

(56) References Cited

U.S. PATENT DOCUMENTS

| | | |
|---|---|---|
| 2005/0288793 A1 | 12/2005 | Dong |
| 2006/0190089 A1 | 8/2006 | Montoya et al. |
| 2013/0035766 A1 | 2/2013 | Meridew |
| 2014/0180431 A1 | 6/2014 | Conway et al. |

OTHER PUBLICATIONS

Zimmer, "Surgical Technique: Trabecular Metal™ Acetabular Revision System Cup-Cage Construct", Zimmer, Inc., p. 1-10, www.zimmer.com (2007).

Zimmer, "Trabecular Metal™ Acetabular Revision System (TMARS)", Zimmer, Inc., p. 1-16, www.zimmer.com (2015).

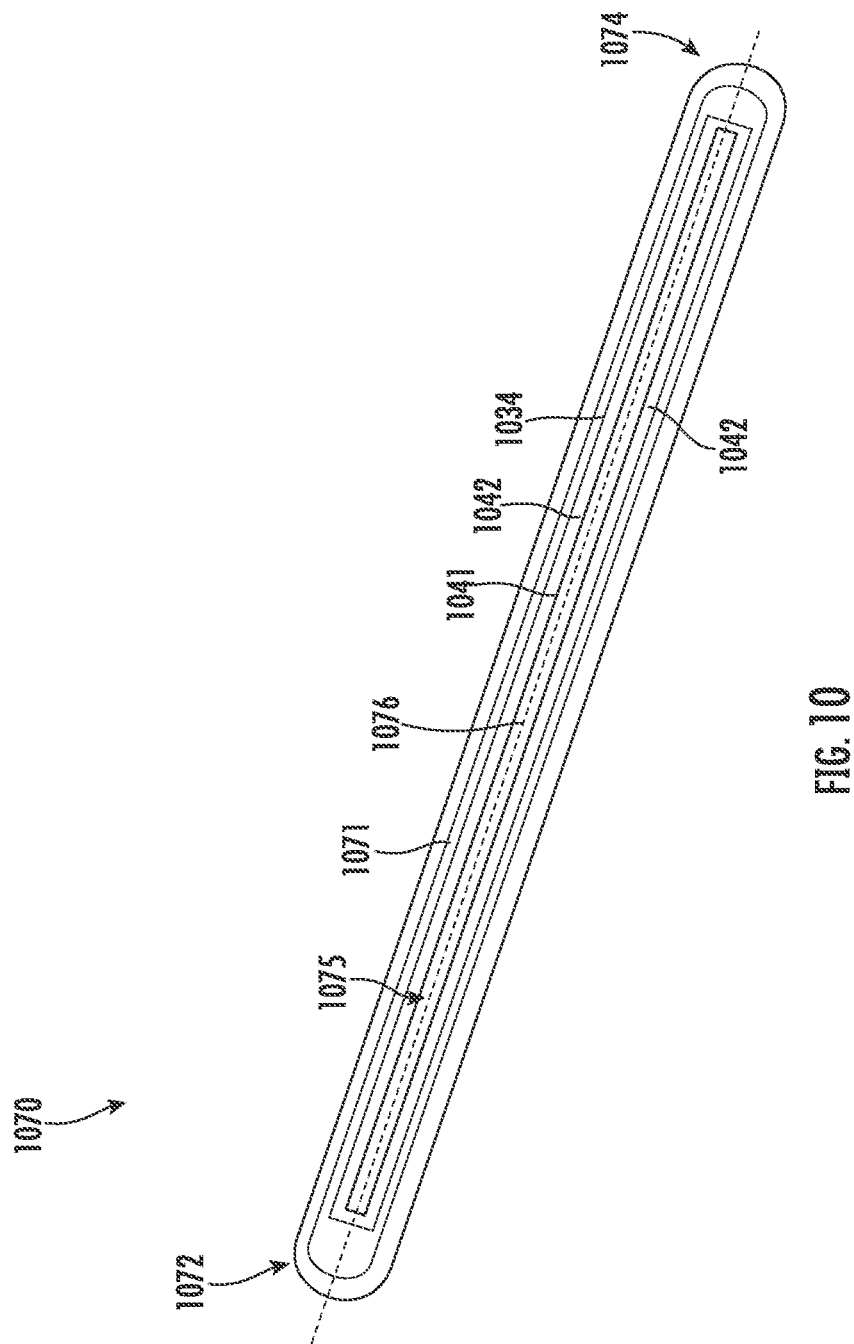

ACETABULAR APPARATUSES FOR HIP REVISION SURGERY

CROSS-REFERENCE TO RELATED APPLICATIONS

This application is a National Phase filing of International Application No. PCT/US2020/024450, filed Mar. 24, 2020, which is a non-provisional of, and claims the benefit of the filing date of, U.S. provisional patent application No. 62/823,343, filed Mar. 25, 2019, entitled "Acetabular Apparatuses for Hip Revision Surgery," each application is incorporated by reference herein in its entirety.

FIELD OF THE DISCLOSURE

The present disclosure relates generally to orthopedic apparatuses and methods to address, for example, acetabular defects, and particularly to acetabular apparatuses for hip revision surgery.

BACKGROUND OF THE DISCLOSURE

Articulating regions of the anatomy can include areas where two bone sections move relative to one another. For example, an acetabulum can provide a region for articulation with a femoral head. The articulating region, however, can become injured or worn, but it can be replaced with various prostheses. Such prostheses can replace the acetabulum, the femoral head, and various other portions of the femur, or other combinations thereof. The replacement of both the acetabulum and the femoral head is generally referred to as a total joint replacement.

Acetabular apparatuses or prosthesis (used interchangeably herein) are one type of prostheses currently used to address acetabular defects in which large portions of the medial wall are missing. Generally speaking, an acetabular apparatus includes an acetabular cage coupled via, for example, an adhesive, to an acetabular cup. Acetabular apparatuses (e.g., cages) often have a central section separating superior and inferior flanges. Current surgical techniques involve bending the superior and inferior flanges in a manner that somewhat matches the patient's iliac and ischial anatomy. The recent introduction and practice of using locking screws in revision acetabular surgery has changed the way surgeons perform these types of reconstructions. For example, inferior locking screws affixed to the ischium and pubis have drastically reduced the need for an inferior flange on the cage. As a result, surgeons sometimes remove the inferior half of the cage altogether, and only affix the superior half and the superior flange of the cage. When a full cage is necessary, surgeons often struggle with flange orientation because the angles of the superior and inferior flanges are fixed and must be forced to match patient anatomy.

Thus, it would be beneficial to provide acetabular apparatuses and methods for using to address the deficiencies of the current art.

SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

The present disclosure provides an acetabular prosthesis including an acetabular cup and an acetabular cage disposed within an interior of the acetabular cup. The acetabular cage may include a central portion including a first section and a second section rotatably coupled together, and a first flange extending from the first section and a second flange extending from the second section. The acetabular prosthesis may further include a fastener extending through each of the first and second sections of the acetabular cup, and the central portion of the acetabular cage.

The present disclosure provides an apparatus including an acetabular cup and an acetabular cage disposed within an interior of the acetabular cup. The acetabular cage may include a central portion including a first section and a second section rotatably coupled together, wherein an end of the first section overlaps with an end of the second section. The acetabular cage may further include a first flange extending from an end of the first section and a second flange extending from an end of the second section. The apparatus may further include a fastener extending through each of the acetabular cup and the overlapped ends of the first and second sections.

The present disclosure provides a prosthesis or implant including, for example, a femoral implant coupled to an acetabular assembly, although it is envisioned that the prosthesis or implant may be any suitable prosthesis or implant. In one embodiment, the acetabular assembly may include an acetabular cup and an acetabular cage disposed within an interior of the acetabular cup. The acetabular cage may include a central portion including a first section and a second section rotatably coupled together, wherein an end of the first section overlaps with an end of the second section. The acetabular cage may further include a first flange extending from an end of the first section and a second flange extending from an end of the second section. The apparatus may further include a fastener extending through each of the acetabular cup and the overlapped ends of the first and second sections.

The present disclosure provides a method including positioning an acetabular cage within an interior of an acetabular cup and positioning a first section of the acetabular cage relative to a second section of the acetabular cage. The first and second sections may be rotatably coupled together. The method may further include securing the first and second sections of the acetabular cage to the acetabular cup.

In one embodiment, an acetabular implant comprising an acetabular cup and an acetabular cage is disclosed. The acetabular cup including a body extending from an equatorial rim to an apex, the body having a generally convex exterior surface and an interior cavity having a generally concave interior surface. The acetabular cage including a central portion disposed within the interior cavity of the acetabular cup, the central portion including a first section and a second section rotatably coupled together, the first section including a first flange arranged and configured to extend from the rim of the acetabular cup, the second section including a second flange arranged and configured to extend from the rim of the acetabular cup.

In one embodiment, the acetabular implant further comprises a fastener extending through each of the acetabular cup and the first and second sections of the acetabular cage, in use, the fastener couples the acetabular cage to the acetabular cup and secures a position of the first section relative to the second section.

In one embodiment, in use, the first and second sections are arranged and configured to rotate with respect to each other to enable adjustable placement of the first and second flanges.

In one embodiment, the first and second sections of the acetabular cage are arranged and configured to slide relative to each other to enable variable placement of the first and second sections within the interior cavity of the acetabular cup.

In one embodiment, the first section of the acetabular cage includes a first end and a second end, the first end of the first section extending from the first flange, the second end of the first section being arranged and configured to be positioned proximate the apex of the acetabular cup. The second section of the acetabular cage includes a first end and a second end, the first end of the second section extending from the second flange, the second end of the second section being arranged and configured to be positioned proximate the apex of the acetabular cup.

In one embodiment, the second end of the first section is arranged and configured to overlap with the second end of the second section so that, in use, a fastener is inserted through an opening formed in the acetabular cup, the first section of the acetabular cage, and the second section of the acetabular cage.

In one embodiment, each of the second ends of the first and second sections of the acetabular cage include a slotted opening arranged and configured to receive the fastener therethrough.

In one embodiment, the second end of the first section includes a first recess and the second end of the second section includes a second recess, the first and second recesses being arranged and configured to provide clearance for the second ends of the first and second sections to slide relative to each other.

In one embodiment, each of the first and second sections of the acetabular cage include one or more cutouts arranged and configured to provide increased flexibility to facilitate bending of the first and second flanges, respectively.

In one embodiment, the acetabular cup includes one or more screw holes extending through the body, the one or more screw holes being arranged and configured to receive a fastener; and each of the first and second sections of the acetabular cage include one or more openings to enable access to one or more screw holes formed in the acetabular cup.

In one embodiment, the acetabular cage includes an exterior convex surface, the exterior convex surface includes one or more surface features adapted and configured to ensure a minimum distance between the interior surface of the cup and the exterior surface of the cage.

In one embodiment, the body of the acetabular cup includes a plurality of screw holes arranged and configured to receive a fastener; and the first and second sections of the acetabular cage each include an elongated slot formed therein, the elongated slot being arranged and configured to align with one or more of the plurality of screw holes formed in the acetabular cup so that a fastener can be inserted through one of the elongated slots and one of the plurality of screw holes.

In one embodiment, the elongated slot formed in the first and second sections of the acetabular cage are arranged and configured so that a head of the fastener engages a perimeter of the elongated slot.

In one embodiment, the elongated slot formed in the first and second sections of the acetabular cage each include a recessed surface defining an inner edge arranged and configured to engage the head of the fastener.

In one embodiment, the recessed surfaces extend along upper and lower portions of the perimeter of the elongated slots so that, in use, the inner edge engages the head of the fastener on opposite sides thereof.

In one embodiment, a method of implanting an acetabular implant into a patient's acetabulum is disclosed. The method comprising preparing the patient's acetabulum as needed; positioning an acetabular cup into the patient's acetabulum; positioning an acetabular cage within an interior cavity of the acetabular cup, the acetabular cage including a first section having a first flange and a second section having a second flange; and adjusting a position of the first and second sections relative to each other to position the first and second flanges in a desired position.

In one embodiment, adjusting a position of the first and second sections relative to each other comprises rotating the first section relative to the second section.

In one embodiment, the method further comprises securing the position of the first and sections of the acetabular cage relative to each other and relative to the acetabular cup.

In one embodiment, securing the position of the first and second sections includes inserting a fastener through an opening formed in the first section, through an opening formed in the second section, and through an opening formed in the acetabular cup.

In one embodiment, the opening formed in the acetabular cup is formed at an apex of the acetabular cup.

In one embodiment, positioning an acetabular cage within an interior cavity of the acetabular cup, the acetabular cage including a first section having a first flange and a second section having a second flange comprises selecting one of the first section and the second section; positioning the selected first or second section into the interior cavity of the acetabular cup; and discarding the other one of the first and second sections of the acetabular cage.

Embodiments of the present disclosure provide numerous advantages. For example, providing an acetabular cage with multiple sections provides ease of use and variability, which enables patient-matched flange orientation (e.g., ilium and ischium). As a result, surgeons can make an intraoperative choice whether to use all or part of the acetabular cage. Furthermore, variability of halves eliminates the need for left and right acetabular cages. When an apex fastener (e.g., screw) is used, rigid or provisional attachment of the acetabular cage and the acetabular cup is enabled. In some embodiments, the apex fastener floats within the half-cages until tightened to the acetabular cup. This permits the acetabular cup and the acetabular cage to be positioned as an assembly. Furthermore, the acetabular cage may be provided with one or more perforations to further aid in removal of one or more parts of the acetabular cage.

Further features and advantages of at least some of the embodiments of the present disclosure, as well as the structure and operation of various embodiments of the present disclosure, are described in detail below with reference to the accompanying drawings.

BRIEF DESCRIPTION OF THE DRAWINGS

By way of example, a specific embodiment of the disclosed device will now be described, with reference to the accompanying drawings, in which:

FIG. 10 shows a perspective view of an example embodiment of a bone plate in accordance with the present disclosure.

Figure 1A:
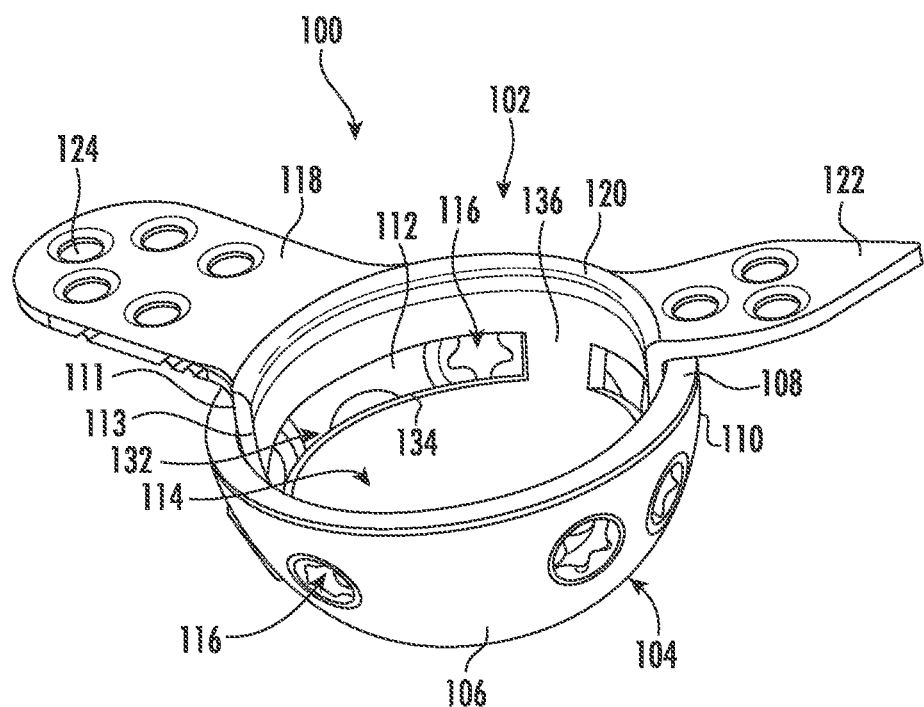
FIG. 1A shows a perspective view of an example embodiment of an apparatus in accordance with the present disclosure.

The drawings are not necessarily to scale. The drawings are merely representations, not intended to portray specific parameters of the disclosure. The drawings are intended to depict example embodiments of the disclosure, and therefore are not to be considered as limiting in scope. In the drawings, like numbering represents like elements.

Furthermore, certain elements in some of the figures may be omitted, or illustrated not-to-scale, for illustrative clarity. The cross-sectional views may be in the form of "slices", or "near-sighted" cross-sectional views, omitting certain background lines otherwise visible in a "true" cross-sectional view, for illustrative clarity. Furthermore, for clarity, some reference numbers may be omitted in certain drawings.

DETAILED DESCRIPTION

Embodiments of an improved acetabular apparatus for hip revision surgery will now be described more fully hereinafter with reference to the accompanying drawings, in which preferred embodiments of the present disclosure are presented. As will be described and illustrated, in some embodiments, the improved acetabular apparatus, implant, assembly, prothesis, etc. (terms used interchangeably herein without the intent to limit) include an acetabular shell or an acetabular cup (terms used interchangeably herein without the intent to limit) and an acetabular cage. In one embodiment, as will be described in greater detail, the cage is adapted and configured to provide variability in flange orientation by incorporating separate superior and inferior cage portions or halves that can be used together as an assembly, or individually. In addition, and/or alternatively, the cage can be coupled, affixed, or the like to the cup by aligning holes formed at the apex of the domes of the cage and the cup. An appropriate fastener, such as a screw, may then be inserted through the aligning holes. The fastener may be used for permanent or temporary holding, for example, while positioning one or more flanges of the cage. Although the various cages described herein include a pair of flanges, a greater or lesser number of flanges may be present in alternative embodiments. For example, it is envisioned that the various cages may include one, three, four, or more flanges.

As will be described and illustrated, in some embodiments, the improved acetabular apparatus includes a cage with surface features adapted and configured to allow for improved cement adhesion between the cup and the cage. The surface features may be provided in any suitable manner now known or hereafter developed including, for example, grooves, recesses, indentations, etc., formed along an exterior surface of the cage. The surface features may be oriented radially, spherically, or both. In various embodiments, the surface features may be arranged and configured to ensure a minimum distance between the cup and the cage for receiving cement.

In addition, and/or alternatively, as will be described and illustrated, in some embodiments, the improved acetabular apparatus includes a cup and a cage including slots or openings (used interchangeably herein without the intent to limit) for coupling the cage to the cup with a fastener. In one example, a slot may be provided along the inside diameter (ID) of the cage. The slot is configured to align with screw holes or slots in the cup so that a screw or multitude of screws could be inserted through the slots/openings formed in the cage and the cup without having to drill through the cage. In one embodiment, the slot formed in the cage may be dimensioned so that the head of the screw engages a perimeter of the slot. As such, the screw will bias the two implants together while engaging host bone.

In another embodiment, the slot or opening formed in the cage may include a recessed surface or tab configured to engage a head of the screw. The head of the screw may also engage locking tabs or pins surrounding one or more openings through the cup as the screw is being inserted into host bone.

Figure 1B:
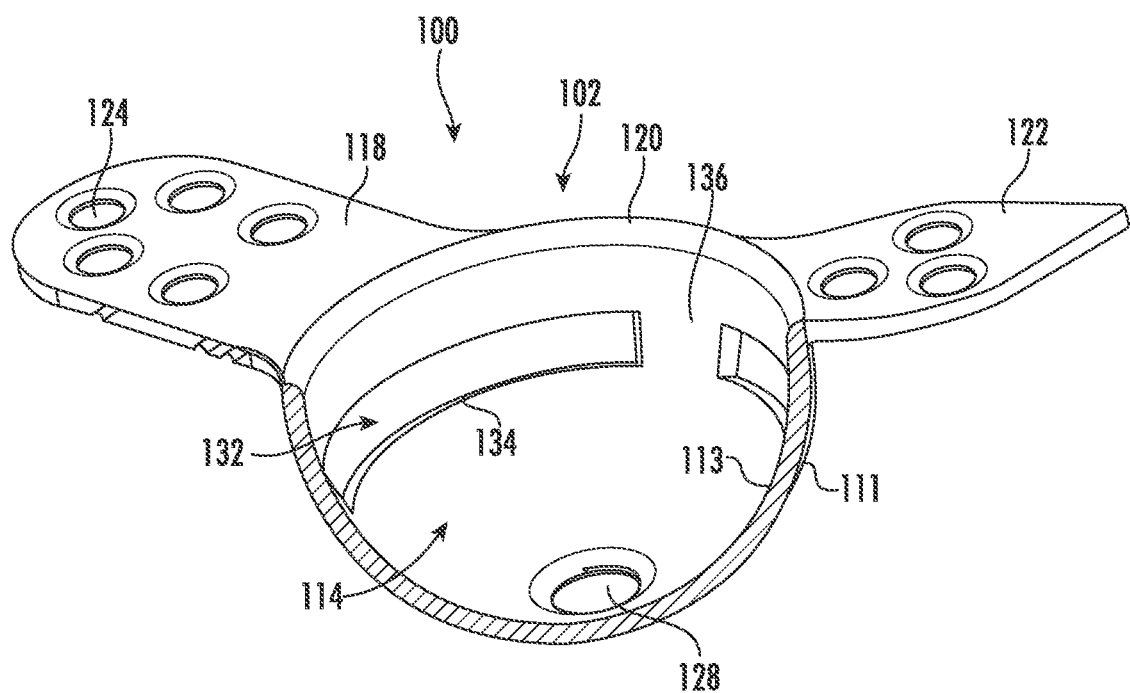
FIG. 1B shows a perspective view of an example embodiment of an acetabular cage of the apparatus of FIG. 1A in accordance with the present disclosure.
Figure 1C:
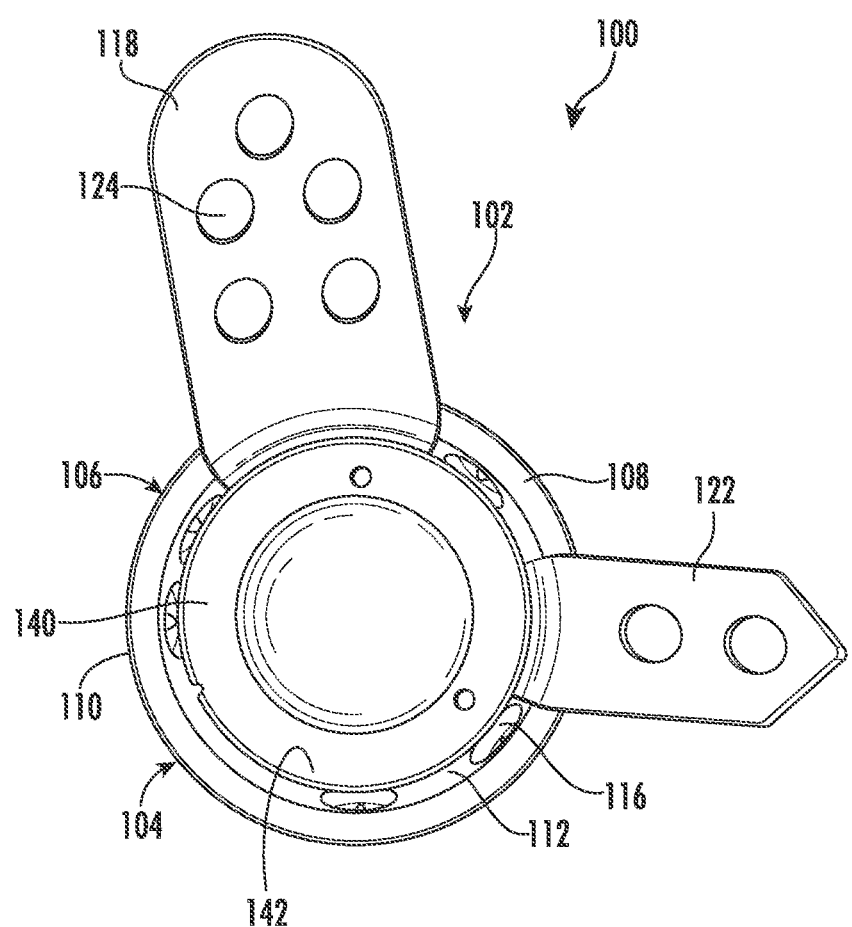
FIG. 1C shows a top view of an example embodiment of the apparatus of FIG. 1A including a liner in accordance with the present disclosure.

Referring to FIGS. 1A-1C a non-limiting example embodiment of an acetabular prosthesis or apparatus 100 is illustrated. As shown, the apparatus 100 may include an acetabular cage (hereinafter "cage") 102 insertable within an interior or interior cavity (used interchangeably herein) of an acetabular cup (hereinafter "cup") 104. The cup 104 may include a hollow body (hereinafter "body") 106 extending from an equatorial rim 108 to an apex or polar end thereof. As shown, the body 106 may define a generally convex exterior surface 110 and a generally concave interior surface 112. The equatorial rim 108 defines a circular opening for receiving a central portion 114 of the cage 102 therein. In some embodiments, cement may be used to secure the cage 102 and the cup 104 together. For example, the cement may be provided between an exterior surface 111 of the central portion 114 of the cage 102 and the interior surface 112 of the cup 104. In other embodiments, the cage 102 and the cup 104 may be mechanically/modularly coupled at one or more interfaces. Embodiments herein are not limited in this context.

As shown, the cup 104 may further include a plurality of openings 116 (also referred to as screw holes herein) through the body 106, between the exterior surface 110 and the interior surface 112. In use, the plurality of openings 116 may receive a fastener (not shown) therein, as will be described in greater detail below. In use, the fasteners extend through the plurality of openings 116 for engagement with host bone (not shown). As will be appreciated by one of ordinary skill in the art, a greater or lesser number of openings 116 may be present in other embodiments. The openings may be locking or non-locking, and, further, locked openings may be fixed or polyaxial.

Although non-limiting, the cup 104 may be made from many different materials including titanium, cobalt chrome, stainless steel, ceramic or other biocompatible material. In some embodiments, the exterior surface 110 may be porous and may be comprised of titanium, cobalt chrome, polymer or other biocompatible material. In addition, the cup 104 may be a combination of different biocompatible materials. For example, the cup 104 may be cobalt chrome with a titanium porous coating on the exterior surface 110. Various manufacturing techniques may be used to manufacture the cup and/or the cage. For example, either implant may be cast and machined or printed, such as by selective laser sintering.

The cage 102 may include a first or superior flange 118 extending from a rim 120 of the cage 102, and a second or inferior flange 122 also extending from the rim 120. In some embodiments, the bone contacting sides of the first and second flanges 118, 122 may be solid or porous. Each of the superior flange 118 and the inferior flange 122 may include a plurality of openings 124 for receiving corresponding fasteners (not shown). The openings 124 may be locking or non-locking screw holes. In use, the fasteners extend through the openings 124 for engagement with host bone (not shown). As will be appreciated by one of ordinary skill in the art, the superior flange 118 and the inferior flange 122 may include a greater or lesser number of openings 124 in other embodiments. Furthermore, the cage 102 is not limited to a pair of flanges (e.g., superior flange 118 and inferior flange 122), and may include a greater or lesser number of flanges in other embodiments. For example, it is envisioned that the cage 102 may include one, three, four, or more flanges.

FIG. 1B further illustrates the cage 102 of the apparatus 100 of FIG. 1A. As shown, the cage 102 may include an apex aperture 128 extending through the body 106, wherein the apex aperture 128 may be aligned with an opening (not shown) formed at the apex of the cup 104. In some embodiments, the apex aperture 128 may be threaded for engagement with a fastener, such as a screw. As will be described in further detail below, the fastener may extend through the apex aperture 128 and the opening of the cup 104 to couple the cage 102 and the cup 104 together.

As further shown, the cage 102 may include one or more slots 132 extending between an exterior surface 111 and the interior surface 113 of the central portion 114. The slots 132 may be defined by a perimeter 134 and separated from one another by one or more support members 136. The slots 132 are operable to receive one or more fasteners therethrough. As better shown in FIG. 1A, the slots 132 facilitate alignment with one or more of the openings 116 though the body 106 of the cup 104. In some embodiments, the slots 132 may allow rotation of the cage 102 relative to the cup 104 prior to fixation while still enabling the slot 132 to be in alignment with the openings 116 formed in the cup 104. Fasteners may extend though the slots 132 and the openings 116 for engagement with host bone. In the case where the fasteners are screws, the perimeter 134 of the slots 132 may be dimensioned to engage a head of each screw. As such, when the screw is further secured into host bone, the cup 104 and the cage 102 are more tightly secured together.

As shown in FIG. 1C, the apparatus 100 may further include a liner 140 within the cage 102. The liner 140 may include a hollow body 142 generally conforming to the inner shape of the cage 102. The liner 140, which may be formed of any suitable material now known or hereafter developed including, for example, polyethylene material such as ultra-high molecular weight polyethylene, a ceramic material, or in some cases, even a metal, may be coupled within the cage 102 to provide an inner bearing surface for receiving, cooperating with, etc., for example, an artificial femoral head in an articulating relationship to track and accommodate the relative movement between the femur and the acetabulum. Although non-limiting, the liner 140 may be secured to the cage 102 by any suitable mechanism now known or hereafter developed including, for example, cement, various mechanical/modular connectors, etc.

Figure 2A:
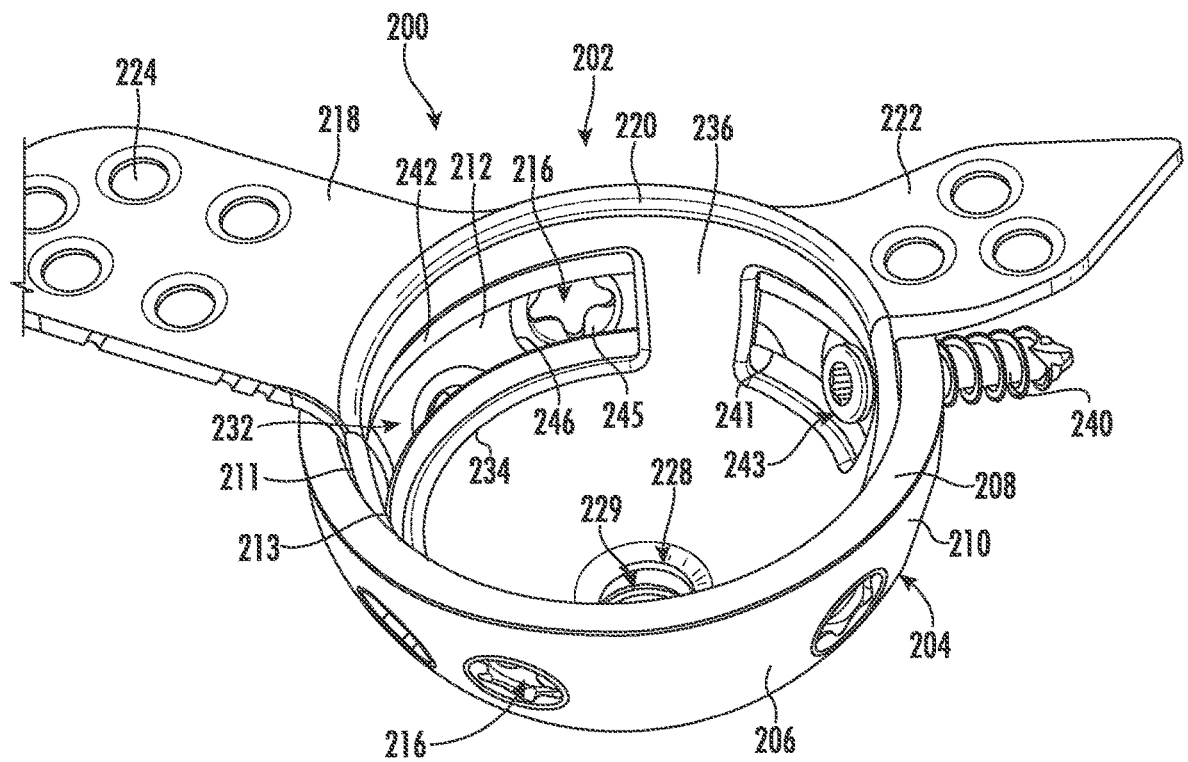
FIG. 2A shows a perspective view of an example embodiment of an apparatus in accordance with the present disclosure.
Figure 2B:
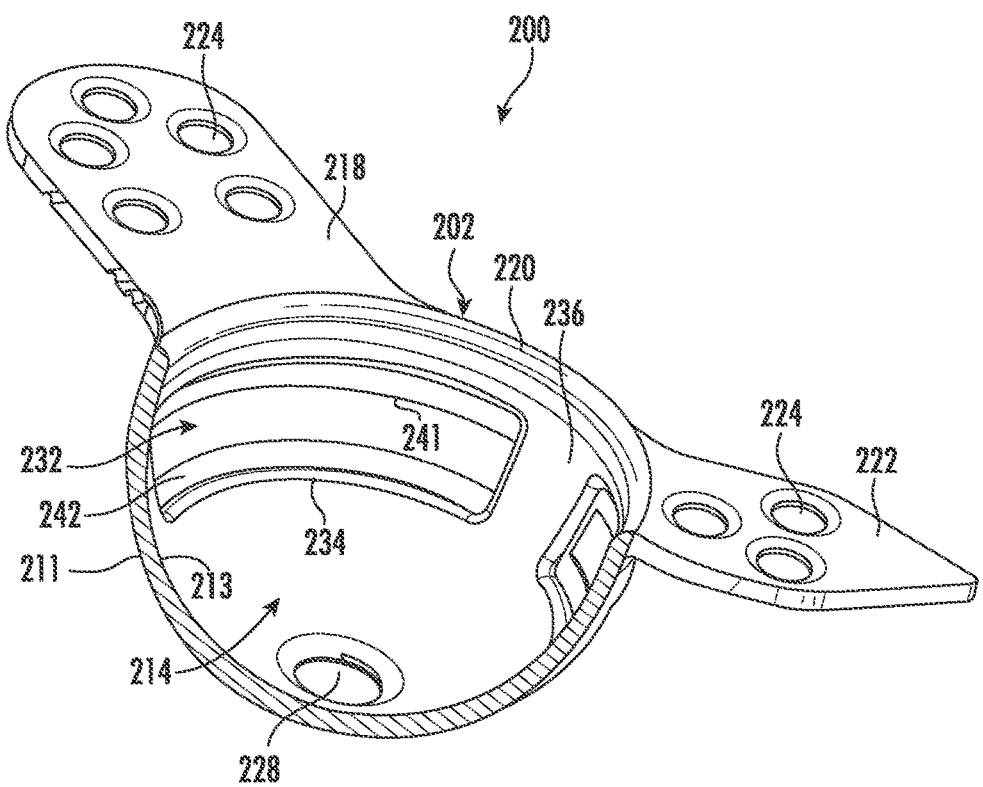
FIG. 2B shows a perspective view of an example embodiment of an acetabular cage of the apparatus of FIG. 2A in accordance with the present disclosure.
Figure 2C:
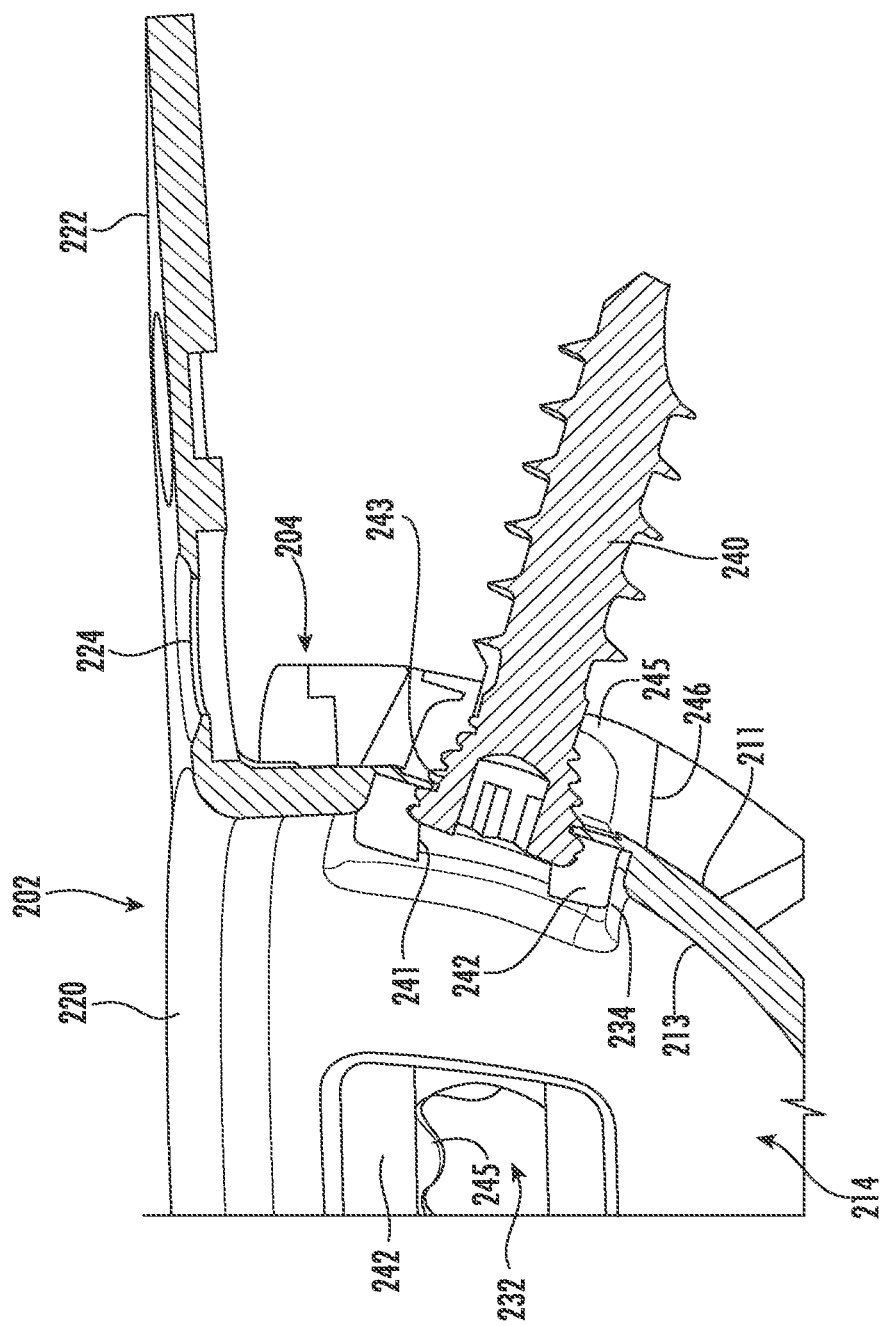
FIG. 2C shows a cross-sectional view of an example embodiment of a fastener in use with the apparatus of FIG. 2A in accordance with the present disclosure.

Referring to FIGS. 2A-2C, a non-limiting example embodiment of an acetabular prosthesis or apparatus 200 is illustrated. As shown, the apparatus 200 may include a cage 202 insertable within an interior of a cup 204. The apparatus 200 may be the same or similar in many aspects to the apparatus 100 shown in FIGS. 1A-1C and described above. As such, only certain features of the apparatus 200 will hereinafter be described for the sake of brevity.

As shown, the cup 204 may include a hollow body 206 extending from an equatorial rim 208 to an apex or polar end thereof. As shown, the body 206 may define a generally convex exterior surface 210 and a generally concave interior surface 212. The equatorial rim 208 defines a circular opening for receiving a central portion 214 of the cage 202 therein. As shown, the cup 204 may further include a plurality of openings 216 through the body 206, for example, between the exterior surface 210 and the interior surface 212.

Although not limited to any particular number of flanges, the cage 202 may include a first or superior flange 218 extending from a rim 220 of the cage 202, and a second or inferior flange 222 also extending from the rim 220. Each of the superior flange 218 and the inferior flange 222 may include a plurality of openings 224 for receiving corresponding fasteners. In use, the fasteners extend through the openings 224 for engagement with host bone.

The cage 202 may include an apex aperture 228 extending through the central portion 214, wherein the apex aperture 228 may be aligned with an opening 229 formed in the apex of the cup 204. In some embodiments, the apex aperture 228 may be threaded for engagement with a fastener, such as a screw, wherein the fastener may extend through the apex aperture 228 of the cage 202 and the opening 229 of the cup 204 to secure the cage 202 and the cup 204 together. Although not shown, the cage 202 may further include a liner provided along an interior surface 213 of the central portion 214 as previously described.

In some embodiments, the cage 202 may include one or more slots 232 extending between an exterior surface 211 and the interior surface 213 of the central portion 214. The slots 232 may be defined by a perimeter 234 and separated from one another by a support member 236. The slots 232 may be aligned with one or more of the openings 216 provided though the body 206 of the cup 204. One or more fasteners 240 may extend though the slots 232 and the openings 216 for engagement with host bone. As shown, the slots 232 may include one or more recessed surfaces 242 configured to engage the fastener 240. Specifically, as better shown in FIG. 2A and FIG. 2C, the recessed surfaces 242 define an inner edge 241 operable to engage a head 243 of the fastener 240. Furthermore, the recessed surfaces 242 may define a locking or non-locking hole.

In the non-limiting embodiment shown, the recessed surfaces 242 extend along upper and lower portions of the perimeter 234 of the slots 232. Thus arranged, the inner edge 241 may therefore engage the head 243 of the fastener 240 on opposite sides. As shown, the recessed surfaces 242 are recessed from the interior surface 213 of the central portion 214 of the cage 202. Said differently, an inner radius of the recessed surfaces 242 is greater than an inner radius of the interior surface 213 taken along a plane perpendicular to a plane defined by the equatorial rim 208. This allows the head 243 of the fastener 240 to be recessed beneath the ID of the cage 202 defined by interior surface 213, thus preventing interference with a liner subsequently implanted inside of the cage 202 as previously described.

The head 243 of the fastener 240 is configured to engage the recessed surfaces 242, which causes the fastener 240 to bias the cage 202 towards the cup 204. The fastener 240 may continue through the openings 216 of the body 206, into host bone. In some embodiments, the head 243 of the fastener 240 is externally threaded, i.e., a locking screw. The openings 216 through the body 206 of the cup 204 may also be threaded for engaging the threaded head 243 of the fastener 240. In other embodiments, the head 243 of the fastener 240 is non-locking.

As shown in FIG. 2A and FIG. 2C, the openings 216 through the body 206 and/or the openings 224 of the superior flange 218 and the inferior flange 222 may include fins 245 or projections that extend radially inward from an inner surface 246 of the openings 216 and into an interior region of the openings 216, and which are configured to engage or cooperate with the head 243 of the fastener 240. In use, the fins 245 engage the head 243 of the fastener 240 in order to secure the fastener 240 at a desired position and at a desired angular orientation within the opening 216. As described in U.S. Pat. No. 10,092,337 entitled Systems and Methods for Using Polyaxial Plates, the entire content of which is hereby incorporated by reference, the openings 216 may be provided with a relatively jagged or undulating inner circumference formed by the inwardly protruding fins 245, and concavities or indentations are formed between adjacent pairs of the fins which extend to a location adjacent the inner surface 246 of the openings 216. Additionally, the inner surface 246 may have a generally round configuration wherein the fins 245 define convex protrusions extending inwardly into the openings 216. However, other shapes and configurations of the openings 216 and/or the flexible fins 245 are also contemplated.

Figure 3A:
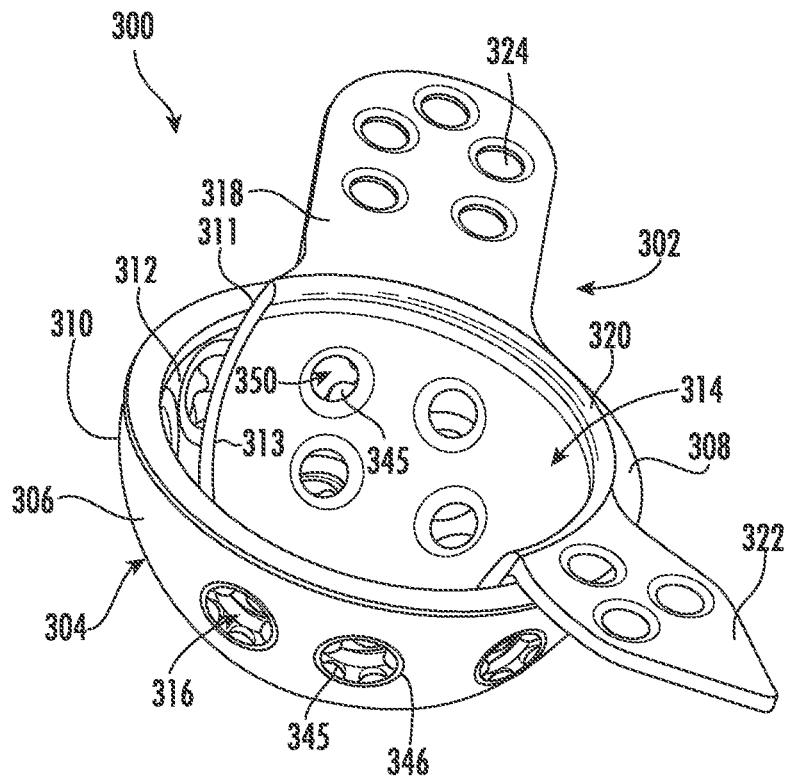
FIG. 3A shows a perspective view of an example embodiment of an apparatus in accordance with the present disclosure.
Figure 3B:
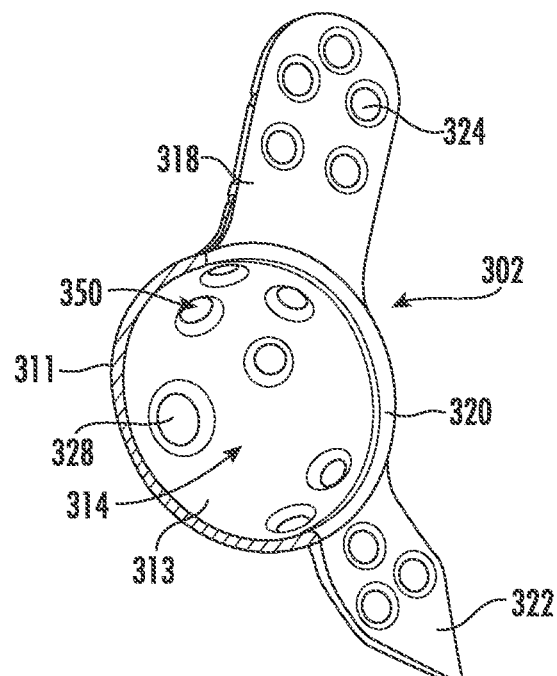
FIG. 3B shows a perspective view of an example embodiment of an acetabular cage of the apparatus of FIG. 3A in accordance with the present disclosure.

Referring to FIGS. 3A-3B, a non-limiting example embodiment of an acetabular prosthesis or apparatus 300 is illustrated. As shown, the apparatus 300 may include a cage 302 insertable within an interior of a cup 304. The apparatus 300 may be the same or similar in many aspects to the apparatuses 100 and 200 described above. As such, only certain features of the apparatus 300 will hereinafter be described for the sake of brevity.

As shown, the cup 304 may include a hollow body 306 extending from an equatorial rim 308 to an apex or polar end thereof. As shown, the body 306 may define a generally convex exterior surface 310 and a generally concave interior surface 312. The equatorial rim 308 defines a circular opening for receiving a central portion 314 of the cage 302 therein. As shown, the cup 304 may further include a plurality of openings 316 through the body 306, for example, between the exterior surface 310 and the interior surface 312.

Although not limited to any particular number of flanges, the cage 302 may include a first or superior flange 318 extending from a rim 320 of the cage 302, and a second or inferior flange 322 also extending from the rim 320. Each of the superior flange 318 and the inferior flange 322 may include a plurality of openings 324 receiving corresponding fasteners (not shown). In use, the fasteners extend through the openings 324 for engagement with host bone.

The cage 302 may include an apex aperture 328 extending through the central portion 314, wherein the apex aperture 328 may be aligned with an opening formed at the apex of the cup 304. In some embodiments, the apex aperture 328 may be threaded for engagement with a fastener, such as a screw, wherein the fastener may extend through the apex aperture 328 of the cage 302 and the opening of the cup 304 to secure the cage 302 and the cup 304 together. Although not shown, the cage 302 may further include a liner provided along an interior surface 313 of the central portion 314 as previously described.

As further shown, the cage 302 may include one or more central apertures 350 extending between an exterior surface 311 and the interior surface 313 of the central portion 314. The central apertures 350 may be aligned with one or more of the openings 316 provided though the body 306 of the cup 304. One or more fasteners (not shown) may extend though the central apertures 350 and the openings 316 for engagement with host bone. As shown in FIG. 3A, the openings 316 through the body 306 may include fins 345 or projections that extend radially inward from an inner surface 346 of the openings 316 and into an interior region thereof, as previously described.

Referring to FIGS. 4A-4D, a non-limiting example embodiment of an acetabular prosthesis or apparatus 400 is illustrated. As shown, the apparatus 400 may include a cage 402 insertable within an interior of a cup 404. The apparatus 400 may be the same or similar in many aspects to apparatuses 100, 200, and 300 described above. As such, only certain features of the apparatus 400 will hereinafter be described for the sake of brevity.

Figure 4A:
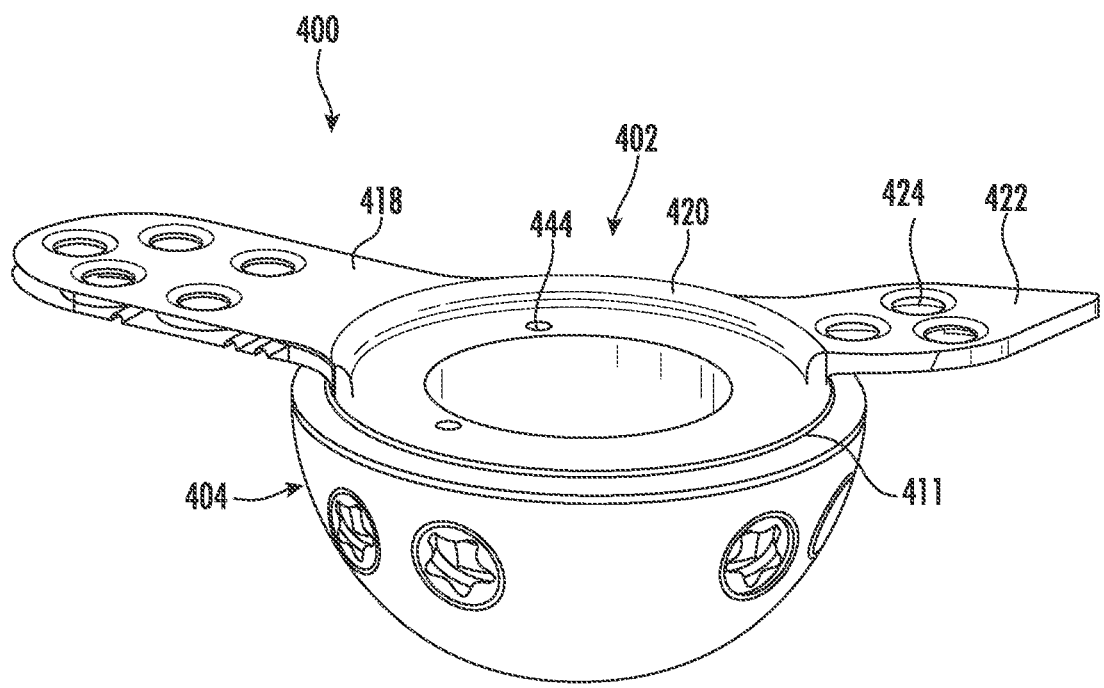
FIG. 4A shows a perspective view of an example embodiment of an apparatus in accordance with the present disclosure.
Figure 4B:
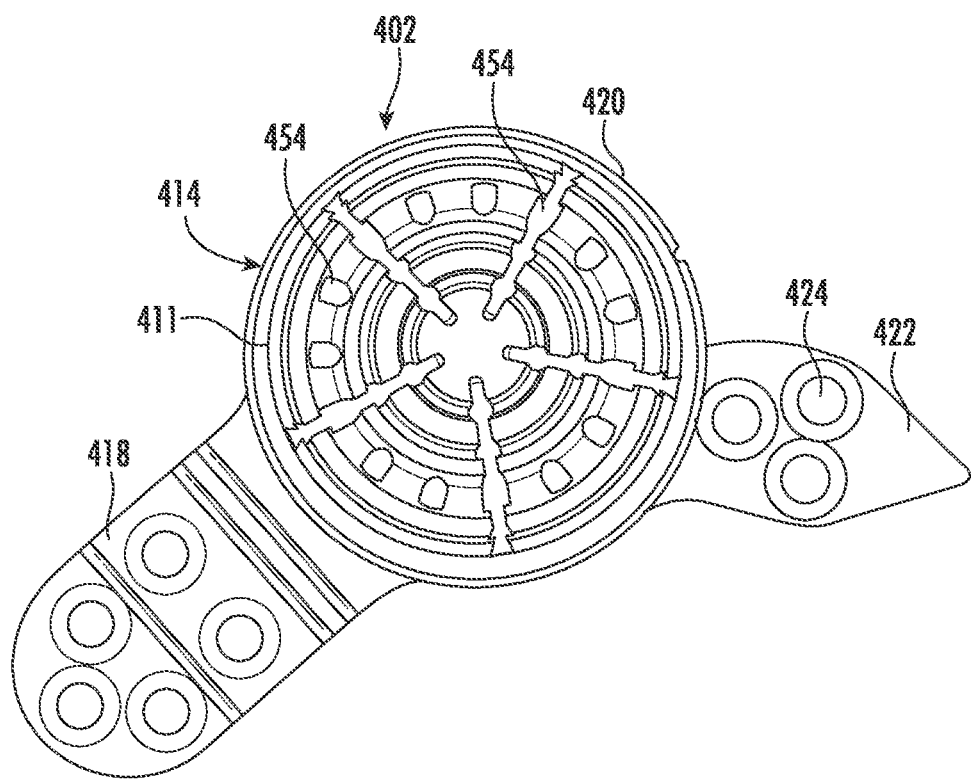
FIG. 4B shows a bottom, perspective view of an example embodiment of an acetabular cage of the apparatus of FIG. 4A, the acetabular cage including a plurality of surface features, in accordance with one aspect of the present disclosure.
Figure 4C:
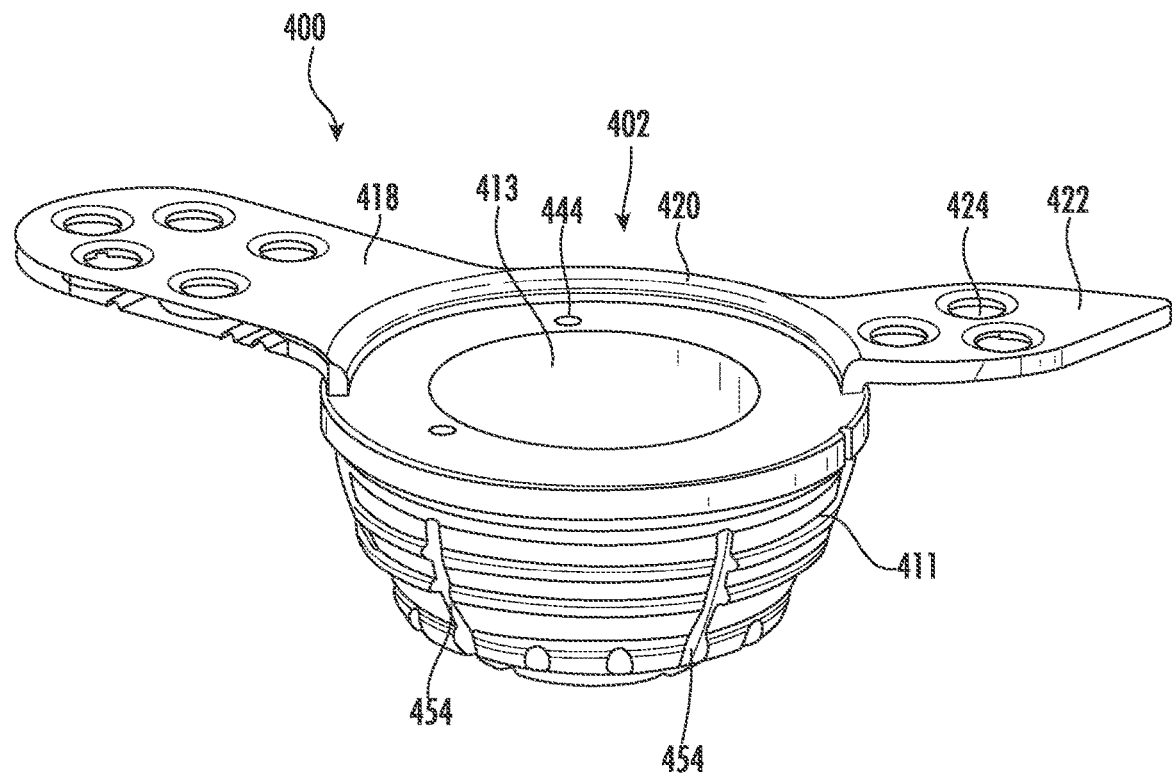
FIG. 4C shows a perspective view of an example embodiment of the acetabular cage of FIG. 4B in accordance with one aspect of the present disclosure.
Figure 4D:
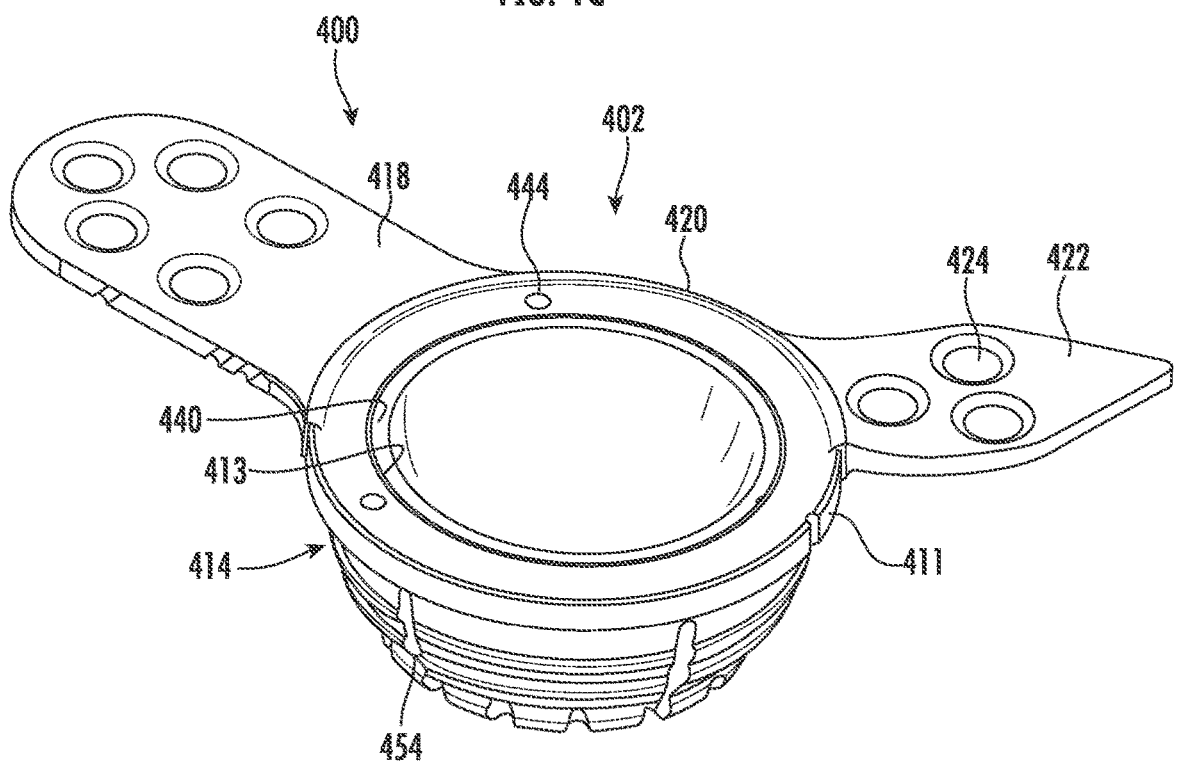
FIG. 4D shows a perspective view of an example embodiment of an acetabular cage of FIG. 4C including a liner in accordance with the present disclosure.

Although not limited to any particular number of flanges, the cage 402 may include a first or superior flange 418 extending from a rim 420 of the cage 402, and a second or inferior flange 422 also extending from the rim 420. Each of the superior flange 418 and the inferior flange 422 may include a plurality of openings 424 receiving a corresponding fastener (not shown). As shown, the cage 402 may further include one or more openings 444 operable to receive an instrument (not shown) for positioning and holding the cage 402. In use, the fasteners extend through the openings 424 for engagement with host bone. Furthermore, as shown in FIG. 4D, the cage 402 may include a liner 440 provided along an interior surface 413 of the central portion 414 as previously described. Although non-limiting, the liner 140 may be secured to the cage 102 by any suitable mechanism now known or hereafter developed including, for example, cement, various mechanical/modular connectors, etc.

As further shown, the cage 402 may include one or more surface features 454 that allow for improved cement adhesion when the cage 402 is coupled to the cup 404. The surface features 454 may be formed along an exterior surface 411 of the cage 402 (e.g., on the outer diameter of the dome portion of the cage 402). In some embodiments, the surface features 454 may be in the form of spherical or radial beads, tubes, grooves, tabs, bumps, valleys, roughened surface, abnormalities, etc. As will be appreciated by one of ordinary skill in the art, the surface features 454 may take on various alternative forms in other embodiments. In various embodiments, the surface features 454 may be arranged and configured to ensure a minimum distance between the cup 404 and the cage 402 for receiving a minimum thickness of, for example, cement. For example, the surface features 454 may be in the form of a ridge, mantle, etc. for ensuring a minimum thickness between the cup 404 and the cage 402.

Figure 5:
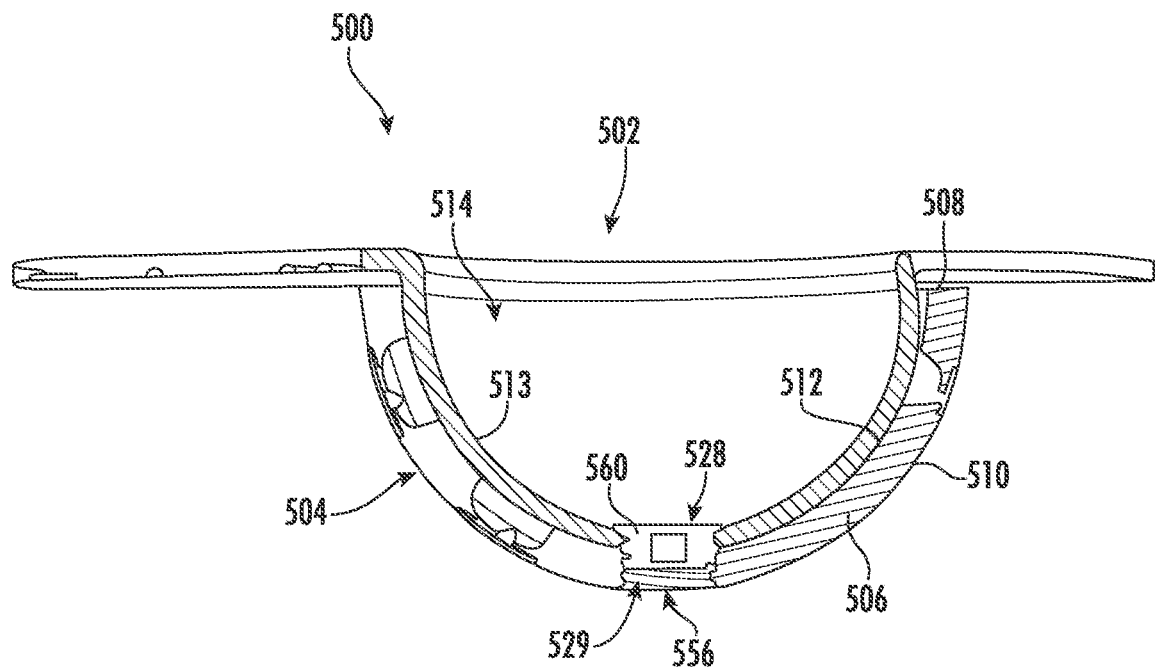
FIG. 5 shows a side cross-sectional view of an example embodiment of an apparatus in accordance with the present disclosure.

Referring to FIG. 5, a non-limiting example embodiment of an acetabular prosthesis or apparatus 500 is illustrated. As shown, the apparatus 500 may include a cage 502 insertable within an interior of a cup 504. The apparatus 500 may be the same or similar in many aspects to apparatuses 100, 200, 300, and 400 described above. As such, only certain features of the apparatus 500 will hereinafter be described for the sake of brevity.

As shown, the cup 504 may include a hollow body 506 extending from an equatorial rim 508 to a polar end or apex 556 thereof. As shown, the body 506 may define a generally convex exterior surface 510 and a generally concave interior surface 512.

The cage 502 may include an apex aperture 528 extending through a central portion 514 thereof, wherein the apex aperture 528 may be aligned with an apex opening 529 formed in the cup 504. As shown, the apex aperture 528 and the apex opening 529 are generally aligned at the apex 556 of the cup 504. In some embodiments, the apex aperture 528 may be threaded for engagement with a fastener 560, such as a threaded screw, wherein the fastener 560 may extend through the apex aperture 528 of the cage 502 and the apex opening 529 of the cup 504 to secure the cage 502 and the cup 504 together. As shown, the fastener 560 may be flush with or recessed below the ID of the cage 502 defined by an interior surface 513, thus preventing interference with a liner (not shown), which may subsequently be implanted inside the cage 502. In other embodiments, the cage 502 and the cup 504 may be secured together using a threaded rod (not shown), which is part of the cup 504, the threaded rod protruding towards the interior of the cup 504.

Figure 6:
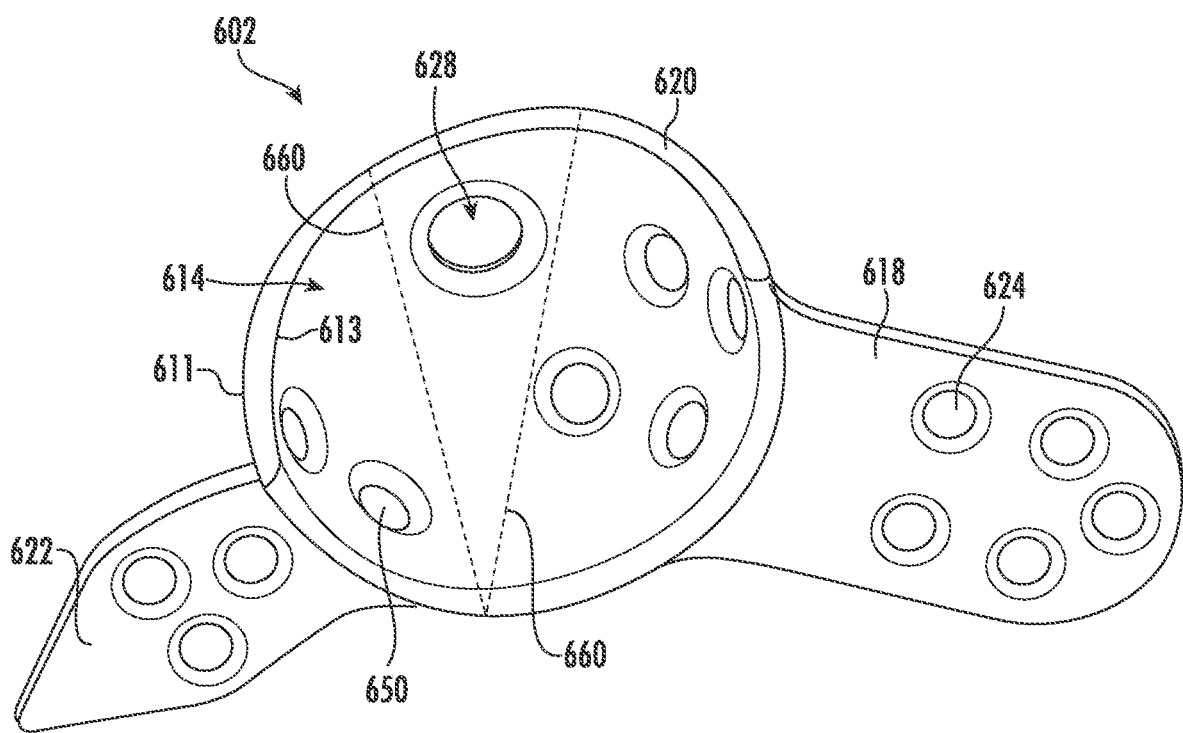
FIG. 6 shows a perspective view of an example acetabular cage in accordance with the present disclosure.

Referring to FIG. 6, a non-limiting example embodiment of an acetabular cage 602 insertable within an interior of a cup (not shown) is illustrated. The cage 602 may be the same or similar in many aspects to the cages 102, 202, 302, 402, and 502 described above. As such, only certain features of the cage 602 will hereinafter be described for the sake of brevity. The cup may be the same or similar in many aspects to the cups 104, 204, 304, 404, and 504 described above.

Although not limited to any particular number of flanges, the cage 602 may include a first or superior flange 618 extending from a rim 620 of the cage 602, and a second or inferior flange 622 also extending from the rim 620. Each of the superior flange 618 and the inferior flange 622 may include a plurality of openings 624 for receiving corresponding fasteners (not shown). In use, the fasteners extend through the openings 624 for engagement with host bone.

The cage 602 may include an apex aperture 628 extending through a central portion 614 thereof, wherein the apex aperture 628 may be aligned with an opening such as, for example, an apex opening, formed in the cup. In some embodiments, the apex aperture 628 may be threaded for engagement with a fastener, such as a screw, wherein the fastener may extend through the apex aperture 628 of the cage 602 and the opening of the cup to secure the cage 602 and the cup together.

As further shown, the cage 602 may include one or more central apertures 650 extending between an exterior surface 611 and an interior surface 613 of the central portion 614. The central apertures 650 may be aligned with one or more of the openings provided through a body of the cup. One or more fasteners (not shown) may extend though the central apertures 650 for engagement with host bone.

The cage 602 may include one or more perforations 660 to permit sectioning of the central portion 614. The perforations 660 may aid users who wish to section part of the central portion 614 and the inferior flange 622, for example. In the non-limiting embodiment shown, two linear perforations 660 may be provided on opposite sides of the apex aperture 628. A user may select between the two perforations 660 depending on whether or not a fastener will be provided through the apex aperture 628. As will be appreciated by one of ordinary skill in the art, the perforations 660 may take on various alternative arrangements in other embodiments. For example, perforations may also be provided though the superior flange 618 and/or the inferior flange 622 to provide increased versatility.

Figure 7A:
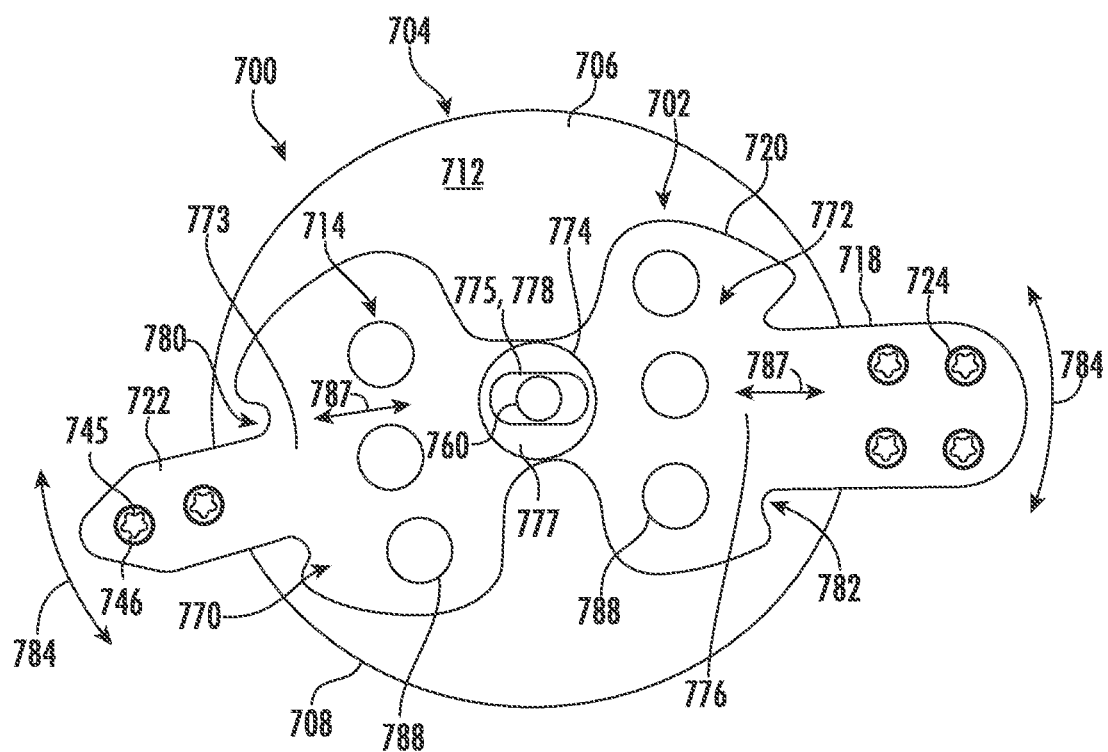
FIG. 7A shows a top view of an example embodiment of an apparatus in accordance with the present disclosure.
Figure 7B:
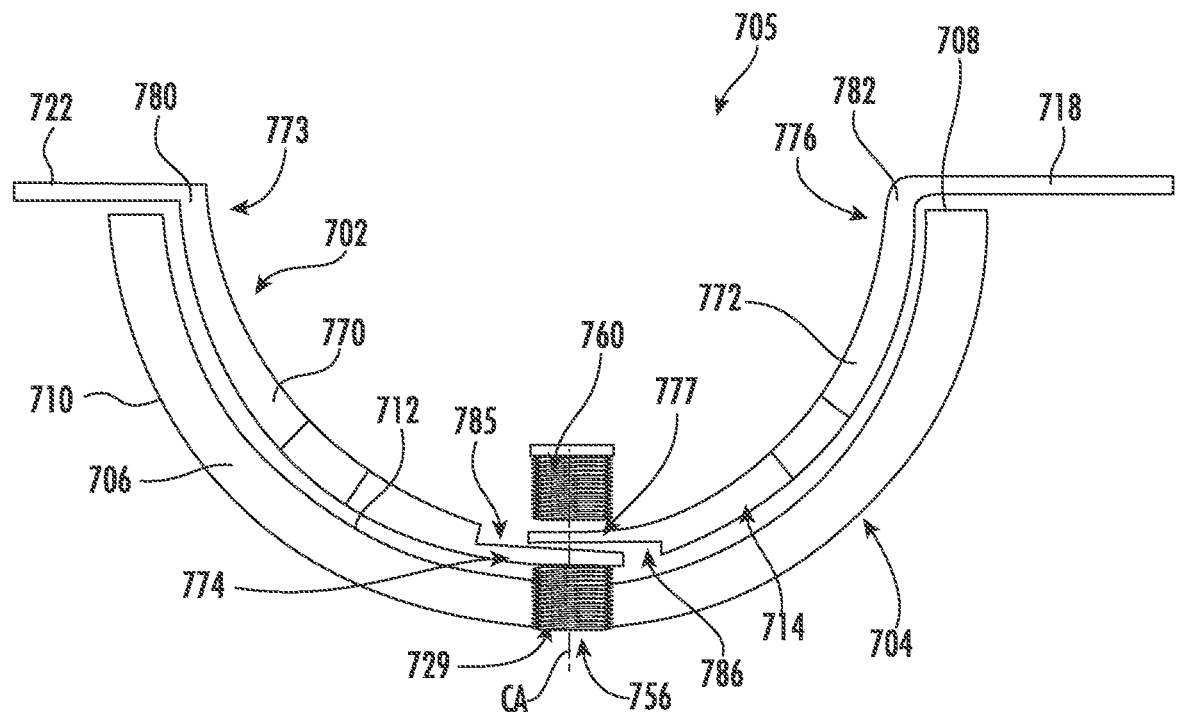
FIG. 7B shows a side cross-sectional view of an example embodiment of the apparatus of FIG. 7A in accordance with the present disclosure.

Referring to FIGS. 7A-7B, a non-limiting example embodiment of an acetabular prosthesis or apparatus 700 is illustrated. As shown, the apparatus 700 may include a cage 702 insertable within an interior of a cup 704. The cup 704 may include a hollow body 706 extending from an equatorial rim 708 to an apex 756 or polar end thereof. As shown, the body 706 may include an interior cavity 705. The body 706 may define a generally convex exterior surface 710 and a generally concave interior surface 712. The equatorial rim 708 defines a circular opening for receiving a central portion 714 of the cage 702 therein. Although not shown, the cup 704 may further include a plurality of openings through the body 706, for example, between the exterior surface 710 and the interior surface 712.

Although not limited to any particular number of flanges, the cage 702 may include a first or superior flange 718 extending from a rim 720 of the cage 702, and a second or inferior flange 722 also extending from the rim 720. Each of the superior flange 718 and the inferior flange 722 may include a plurality of openings 724 receiving corresponding fasteners. In use, the fasteners, which may be locking or non-locking, extend through the openings 724 for engagement with host bone.

As shown, the cage 702 may include two or more sections joined together, such as a first section 770 and a second section 772. It should be understood that although the example embodiment will be described and illustrated as including two sections, it is envisioned that the cage 702 may include three, four, or more sections with each section including one or more flanges.

As illustrated in the example embodiment, the first section 770 may include a first end 773 extending from the inferior flange 722, and a second end 774 proximate the apex 756 of the cup 704. One or more cutouts 780 may be provided at the intersection of the first end 773 and the inferior flange 722 for increased flexibility. The second end 774 may include a slotted opening 775 configured to receive a fastener 760 therethrough.

The second section 772 may include a first end 776 extending from the superior flange 718, and a second end 777 proximate the apex 756 of the cup 704. One or more cutouts 782 may be provided at the intersection of the first end 776 and the superior flange 718 for increased flexibility. The second end 777 may include a slotted opening 778 configured to receive the fastener 760 therethrough. As shown, the second end 777 of the second section 772 may overlap with the second end 774 of the first section 770, or vice-versa. As such, the first and second sections 770, 772 may rotate (e.g., as shown by arrows 784) with respect to one another about a central axis 'CA' extending through the slotted openings 775, 778 and through the fastener 760 (e.g., the first and second sections 770, 772 are movable relative to each other prior to tightening of the fastener 760 so that the superior and inferior flanges 718, 722 can be positioned as desired). The overlap of respective second ends 774, 777 may keep the first and second sections 770, 772 in a same plane, while also minimizing thickness of the cage 702. Alternatively, and/or in addition, the openings such as, for example, opening 778 may be used to facilitate cement adhesion between the cage 702 and the cup 704 as cement may be injected into the opening.

Furthermore, as best shown in FIG. 7B, the first section 770 and the second section 772 may be arranged and configured to enable the first and second sections to move, slide, etc. relative to each other as represented by arrows 787. For example, in one embodiment, the first section 770 may include a first cutout or recess 785 and the second section 772 may include a second cutout or recess 786. The first and second cutouts or recesses 785, 786 may be centrally located. The first cutout or recess 785 and the second cutout or recess 786 provide clearance for the second ends 774, 777 to slide relative to one another, for example, in a direction shown by arrows 787. In use, the slotted openings 775, 778 and the first and second cutouts or recesses 785, 786 facilitate increased flexibility in positioning the first and second sections 770, 772 relative to each other, and relative to the cup 704. For example, the slotted openings 775, 778 and the first and second cutouts or recesses 785, 786 allow better conformity of the outer diameter of the cage 702 to the inner diameter of the cup 704 and allow one cage 702 to fit multiple different cups 704 (e.g., a single cage 702 may fit three different cup 704 sizes).

In use, the first and second sections 770, 772 may be arranged into a desired positioned, and then fixed together in place by the fastener 760. The slotted openings 775 and 778 may be threaded or non-threaded. As shown, the slotted openings 775, 778 are aligned with an opening 729 of the cup 704, wherein the fastener 760 may extend through the slotted openings 775, 778 and though the opening 729 of the cup 704 to secure the cage 702 and the cup 704 together. In the non-limiting embodiment shown, the openings 724 of the superior flange 718 and the inferior flange 722 may include fins 745 or projections that extend radially inward from an inner surface 746 of the openings 724 and into an interior region thereof. The fins 745 are configured to engage or cooperate with a head of a fastener (not shown) in order to secure the fastener at a desired position and at a desired angular orientation within the opening 724. In some embodiments, the openings 724 may be provided with a relatively jagged or undulating inner circumference formed by the inwardly protruding fins 745, and concavities or indentations are formed between adjacent pairs of the fins which extend to a location adjacent the inner surface 746 of the openings 724. Additionally, the inner surface 746 may have a generally round configuration wherein the fins 745 define convex protrusions extending inwardly into the openings 724. However, other shapes and configurations of the openings 724 and/or the flexible fins 745 are also contemplated.

In some embodiments, each of the first and second sections 770, 772 may include one or more openings or windows 788. In use, the openings or windows 788 enable access to one or more screw holes (not shown) formed in the cup 704. Although shown as a series of circles, other configurations for the windows 788 are possible in various alternative embodiments. For example, in one embodiment, a single, larger opening or window 788 may be formed in each of the first and second sections 770, 772. It should also be understood that while the openings or windows 788 are illustrated as being circular, the openings or windows may have any shape including, for example, square, rectangular, trapezoidal, of the like. Moreover, the openings or windows on the first section 770 need not be the same as the openings or windows on the second section 772.

Figure 8:
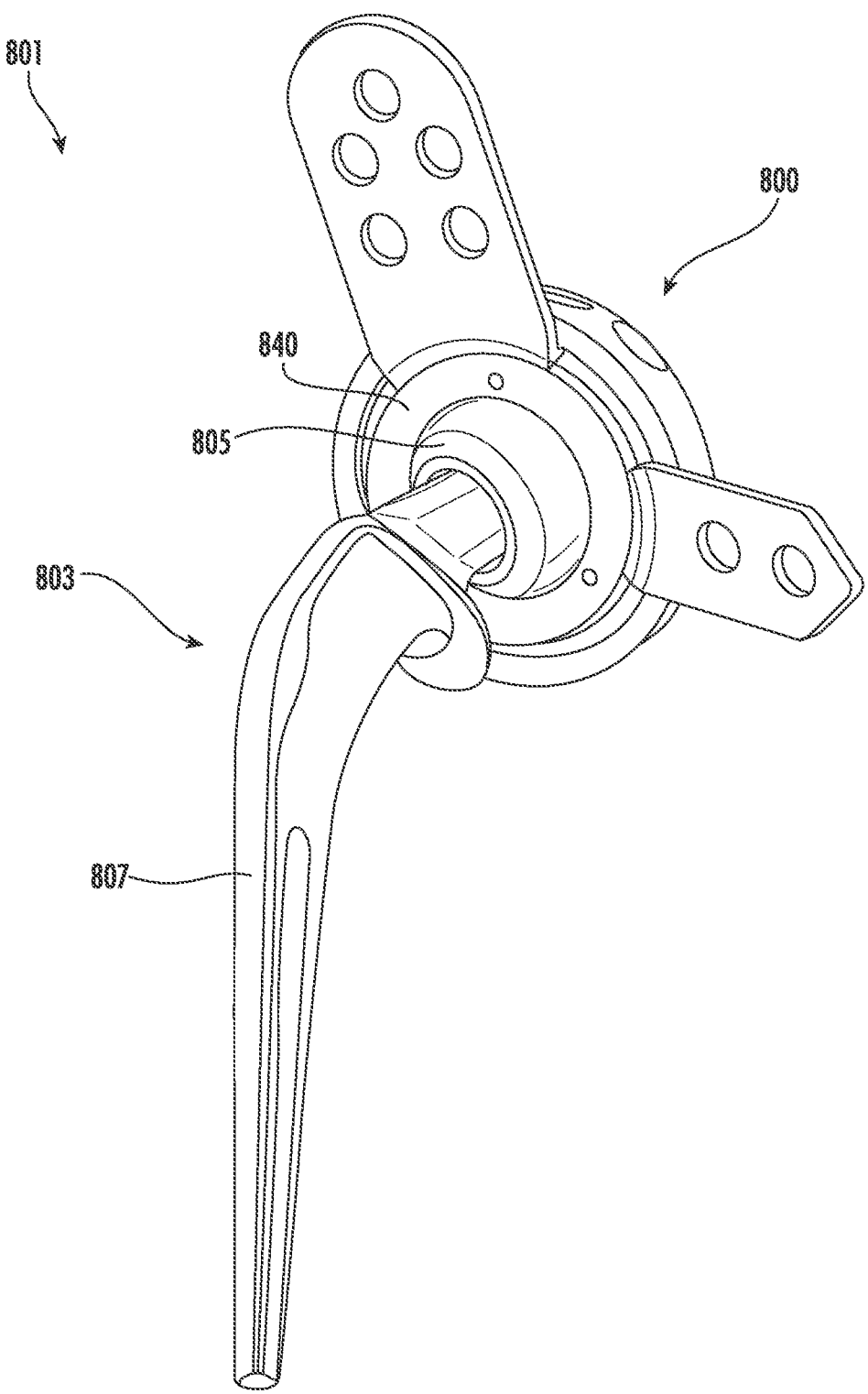
FIG. 8 shows a perspective view of an example prosthesis in accordance with the present disclosure.

As demonstrated in FIG. 8, the apparatuses described herein may be part of a prosthesis 801, such as a hip implant. The prosthesis 801 may include a femoral implant 803 with a prosthetic femoral head 805 extending from a femoral stem 807. As shown, the femoral head 805 may be inserted within an acetabular prosthesis or apparatus 800. The apparatus 800 may be the same or similar in many aspects to apparatuses 100, 200, 300, 400, 500, 600, and 700 described above. When the femoral implant 803 is coupled with the apparatus, the femoral head 805 may rotate/articulate relative to an inner surface of a liner 840 of the apparatus 800.

Figure 9:
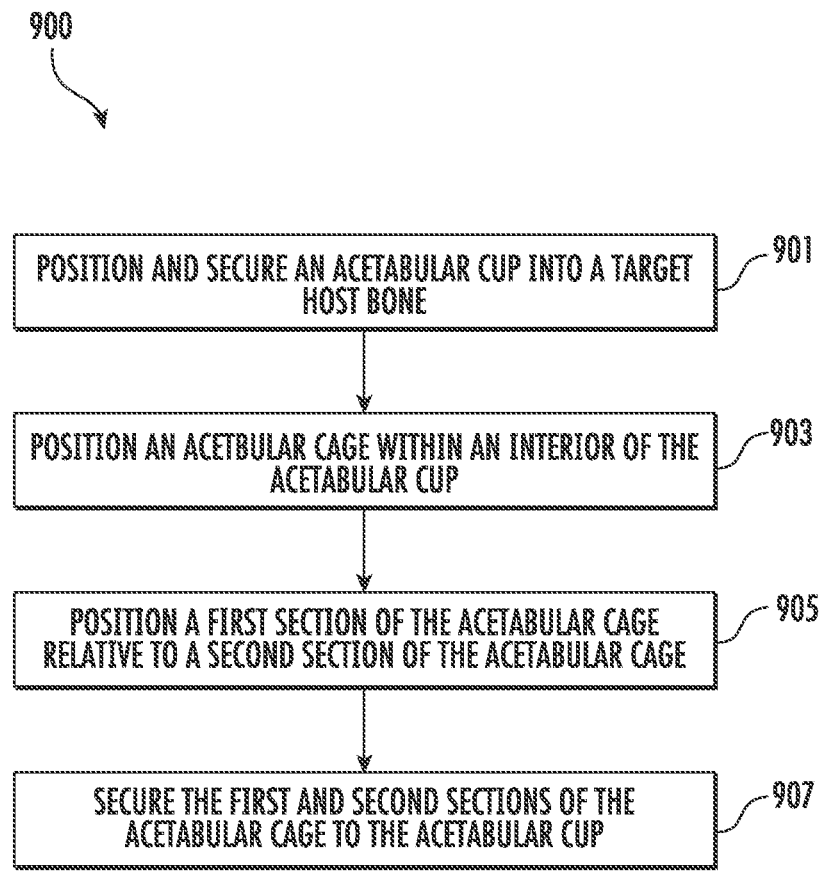
FIG. 9 depicts a method in accordance with embodiments of the disclosure.

Referring to FIG. 9, a non-limiting example embodiment of a method 900 is illustrated. In use, the acetabulum may be exposed and assessed identifying the location of quality bone. As needed, the acetabulum may be reconstructed using various instruments such as, impactors, reamers, etc. Next, at block 901, the method 900 may include positioning and securing an acetabular cup into a target host bone. The acetabular cup may be impacted into the target host bone and, in some embodiments, one or more optional fasteners may be inserted thru the cup and into the host bone. At block 903, the method 900 may include positioning an acetabular cage within an interior of the acetabular cup. In use, the inferior and superior flanges of the cage may be properly positioned and, in some embodiments, the cage may be properly contoured as needed. In some embodiments, the cup may include a hollow body extending from an equatorial rim to an apex or polar end thereof. Although non-limiting, the body may define a generally convex exterior surface and a generally concave interior surface. The equatorial rim defines a circular opening for receiving a central portion of the cage therein. The cup may further include a plurality of openings through the body, between the exterior surface and the interior surface. In use, the plurality of openings may receive corresponding fasteners.

In some embodiments, the cage may include a superior flange extending from a rim of the cage, and an inferior flange also extending from the rim. Each of the superior flange and the inferior flange may include a plurality of openings receiving corresponding fasteners. In use, the fasteners extend through the openings for engagement with host bone.

At block 905, if the acetabular cage includes first and second movable sections, the method 900 may include positioning a first section of the acetabular cage relative to a second section of the acetabular cage. The first and second sections may be rotatably coupled together. In some embodiments, the first section may include a first end extending from the inferior flange, and a second end proximate the apex of the cup. The second end of the first section may include an opening configured to receive a fastener therethrough. The second section may include a first end extending from the superior flange, and a second end proximate the apex of the cup. The second end of the second section may include an opening configured to also receive the fastener therethrough. In some embodiments, the second end of the second section may overlap with the second end of the first section. As such, the first and second sections may rotate with respect to one another about a central axis extending through the openings and through the fastener.

At block 907, the method 900 may further include securing the acetabular cage to the cup. For example, the first and second sections of the acetabular cage may be coupled to the acetabular cup. In other embodiments, the acetabular cage may be a single contiguous component, which is secured to the cup. In some embodiments, the fastener extending through the first and second sections of the acetabular cage and an opening of the cup is tightened. Once tightened, the first and second sections of the acetabular cage and the acetabular cup are fixed into position. The acetabular cage may then be secured to host bone.

After the cage has been properly positioned relative to the cup, cement may be inserted, injected, or the like into the cage to, inter alia, facilitate better coupling between the cage and the cup. Alternatively, it should be appreciated that the cement may be inserted, injected, or the like prior to insertion of the cage into the cup. It should be appreciated that the cement may be inserted, injected, or the like into the cage before, after, or both in relation to timing of cage placement. Finally, if necessary, a liner may be inserted into the cage.

Referring to FIG. 10, a non-limiting example embodiment of an implant 1070 is illustrated. The implant 1070 may be a bone plate for coupling to a patient's bone. The implant 1070 may include an outer surface 1071, a bone contacting surface (not shown), a first end 1072, a second end 1074, and a central longitudinal axis 1076. As shown, the implant 1070 also includes one or more slots 1075. The one or more slots 1075 may extend through the implant 1070, for example, from the upper surface 1071 to the bone contacting surface. In some embodiments, the implant 1070 can have a variety of different shapes and sizes. For example, one or more sections of the implant 1070 can have contours or curves that generally correspond to similar contours or curves of a portion of the bone against which the bone contacting surface of the implant 1070 can abut or otherwise be located at an adjacent position. Further, the implant 1070 can be constructed from a variety of materials, including, for example, stainless steel, titanium, polymers, and/or ceramics, among other materials.

As shown, similar to the construction and operation of the slot 232 shown described in connection with FIGS. 2A-2C, the slot 1075 may be defined by a perimeter 1034 and one or more recessed surfaces 1042. During use, one or more fasteners (not shown) may extend though the slot 1075 for engagement with host bone. Specifically, the recessed surfaces 1042 define an inner edge 1041 operable to engage a head of a fastener. In various embodiments, the recessed surfaces 1042 may define a locking or non-locking hole.

In the non-limiting embodiment shown, the recessed surfaces 1042 extends along opposite sides of the central longitudinal axis 1076. Thus arranged, the inner edge 1041 may therefore engage the head of the fastener on opposite sides (as generally shown in FIG. 2C). In some embodiments, the slot 1075 is dimensioned to allow the head of the fastener to be recessed below the outer surface 1071 of the implant 1070.

Although the implant 1070 is illustrated and described in the context of a bone plate, embodiments herein are not so limited. The slot 1075 may be employed with a variety of different types of medical implants.

While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments, but that it has the full scope defined by the language of the following claims, and equivalents thereof. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

The foregoing discussion has been presented for purposes of illustration and description and is not intended to limit the disclosure to the form or forms disclosed herein. For example, various features of the disclosure are grouped together in one or more embodiments or configurations for the purpose of streamlining the disclosure. However, it should be understood that various features of the certain embodiments or configurations of the disclosure may be combined in alternate embodiments, or configurations.

As used herein, an element or step recited in the singular and proceeded with the word "a" or "an" should be understood as not excluding plural elements or steps, unless such exclusion is explicitly recited. Furthermore, references to "one embodiment" of the present disclosure are not intended to be interpreted as excluding the existence of additional embodiments that also incorporate the recited features.

The phrases "at least one", "one or more", and "and/or", as used herein, are open-ended expressions that are both conjunctive and disjunctive in operation. The terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure.

Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. All rotational references describe relative movement between the various elements. Identification references (e.g., primary, secondary, first, second, third, fourth, etc.) are not intended to connote importance or priority but are used to distinguish one feature from another. The drawings are for purposes of illustration only and the dimensions, positions, order and relative to sizes reflected in the drawings attached hereto may vary.

The invention claimed is:

1. An acetabular implant comprising:
an acetabular cup including a body extending from an equatorial rim to an apex, the body having a generally convex exterior surface and an interior cavity having a generally concave interior surface; and
an acetabular cage including a central portion disposed within the interior cavity of the acetabular cup, the central portion including a first section and a second section rotatably coupled together, the first section including a first flange arranged and configured to extend from the rim of the acetabular cup, the second section including a second flange arranged and configured to extend from the rim of the acetabular cup.

2. The acetabular implant of claim 1, further comprising a fastener extending through each of the acetabular cup and the first and second sections of the acetabular cage, in use, the fastener couples the acetabular cage to the acetabular cup and secures a position of the first section relative to the second section.

3. The acetabular implant of claim 1, wherein, in use, the first and second sections are arranged and configured to rotate with respect to each other to enable adjustable placement of the first and second flanges.

4. The acetabular implant of claim 3, wherein the first and second sections of the acetabular cage are arranged and configured to slide relative to each other to enable variable placement of the first and second sections within the interior cavity of the acetabular cup.

5. The acetabular implant of claim 1, wherein:
the first section of the acetabular cage includes a first end and a second end, the first end of the first section extending from the first flange, the second end of the first section being arranged and configured to be positioned proximate the apex of the acetabular cup; and
the second section of the acetabular cage includes a first end and a second end, the first end of the second section extending from the second flange, the second end of the second section being arranged and configured to be positioned proximate the apex of the acetabular cup.

6. The acetabular implant of claim 5, wherein the second end of the first section is arranged and configured to overlap with the second end of the second section so that, in use, a fastener is inserted through an opening formed in the acetabular cup, the first section of the acetabular cage, and the second section of the acetabular cage.

7. The acetabular implant of claim 6, wherein each of the second ends of the first and second sections of the acetabular cage include a slotted opening arranged and configured to receive the fastener therethrough.

8. The acetabular implant of claim 7, wherein the second end of the first section includes a first recess and the second end of the second section includes a second recess, the first and second recesses being arranged and configured to provide clearance for the second ends of the first and second sections to slide relative to each other.

9. The acetabular implant of claim 5, wherein each of the first and second sections of the acetabular cage include one or more cutouts arranged and configured to provide increased flexibility to facilitate bending of the first and second flanges, respectively.

10. The acetabular implant of claim 1, wherein:
the acetabular cup includes one or more screw holes extending through the body, the one or more screw holes being arranged and configured to receive a fastener; and
each of the first and second sections of the acetabular cage include one or more openings to enable access to one or more screw holes formed in the acetabular cup.

11. The acetabular implant of claim 1, wherein the acetabular cage includes an exterior convex surface, the exterior convex surface includes one or more surface features adapted and configured to ensure a minimum distance between the interior surface of the cup and the exterior surface of the cage.

12. The acetabular implant of claim 1, wherein:
the body of the acetabular cup includes a plurality of screw holes arranged and configured to receive a fastener; and
the first and second sections of the acetabular cage each include an elongated slot formed therein, the elongated slot being arranged and configured to align with one or more of the plurality of screw holes formed in the acetabular cup so that a fastener can be inserted through one of the elongated slots and one of the plurality of screw holes.

13. The acetabular implant of claim 12, wherein the elongated slot formed in the first and second sections of the acetabular cage are arranged and configured so that a head of the fastener engages a perimeter of the elongated slot.

14. The acetabular implant of claim 13, wherein the elongated slot formed in the first and second sections of the acetabular cage each include a recessed surface defining an inner edge arranged and configured to engage the head of the fastener.

15. The acetabular implant of claim 14, wherein the recessed surfaces extend along upper and lower portions of the perimeter of the elongated slots so that, in use, the inner edge engages the head of the fastener on opposite sides thereof.

16. A method of implanting an acetabular implant into a patient's acetabulum, the method comprising:
preparing the patient's acetabulum as needed;
positioning an acetabular cup into the patient's acetabulum;
positioning an acetabular cage within an interior cavity of the acetabular cup, the acetabular cage including a first section having a first flange and a second section having a second flange; and
adjusting a position of the first and second sections relative to each other to position the first and second flanges in a desired position.

17. The method of claim 16, wherein adjusting a position of the first and second sections relative to each other comprises rotating the first section relative to the second section.

18. The method of claim 17, further comprising securing the position of the first and sections of the acetabular cage relative to each other and relative to the acetabular cup.

19. The method of claim 18, wherein securing the position of the first and second sections includes inserting a fastener through an opening formed in the first section, through an opening formed in the second section, and through an opening formed in the acetabular cup.

20. The method of claim 19, wherein the opening formed in the acetabular cup is formed at an apex of the acetabular cup.

21. The method of claim 16, wherein positioning an acetabular cage within an interior cavity of the acetabular cup, the acetabular cage including a first section having a first flange and a second section having a second flange comprises
selecting one of the first section and the second section;

positioning the selected first or second section into the interior cavity of the acetabular cup; and discarding the other one of the first and second sections of the acetabular cage.

* * * * *